United States Patent [19]

Mount

[11] 4,356,486

[45] Oct. 26, 1982

[54] TELEMETERING SYSTEM FOR OPERATING ROOM AND THE LIKE

[75] Inventor: Bruce E. Mount, Diamond Bar, Calif.

[73] Assignee: Medimetric Company, Los Angeles, Calif.

[21] Appl. No.: 133,276

[22] Filed: Mar. 24, 1980

Related U.S. Application Data

[62] Division of Ser. No. 956,593, Nov. 1, 1978.

[51] Int. Cl.³ .................... G08C 19/04; G08C 19/16
[52] U.S. Cl. ............... 340/870.38; 128/903; 324/62; 324/65 R; 340/870.17; 340/870.21
[58] Field of Search ............ 340/870.11, 870.13, 340/870.17, 870.28, 870.38, 870.21, 584, 599; 73/362 R, 362 AR, 360; 324/62, 63, 65 R; 128/903, 904, 672, 680; 179/175.3 F

[56] References Cited

U.S. PATENT DOCUMENTS

| | | | |
|---|---|---|---|
| 2,098,227 | 11/1937 | Chauveau | 340/870.38 |
| 2,630,007 | 3/1953 | Howe et al. | 340/870.38 |
| 3,582,921 | 6/1971 | Krieger | 340/870.17 |
| 3,922,490 | 11/1975 | Pettis | 340/870.38 |
| 3,961,317 | 6/1976 | De Brem et al. | 340/870.38 |
| 4,025,736 | 5/1977 | Chlupsa | 340/870.38 |

Primary Examiner—James J. Groody

[57] ABSTRACT

A system for telemetering data from a patient to a monitor permitting direct connection of patient's sensors and transducers to the monitor and permitting telemetering by radio or wire without requiring changes in transducer or monitor design or adjustment or calibration. A telemetering system which presents to the monitor a variable resistance identical to the varying resistance produced by a transducer at the patient. A temperature transmission channel wherein a thermistor resistance is connected in a bridge circuit which is balanced by successive trials of a set of resistors digitally selected by a counter and comparator. The code for the selected value which produces balance is transmitted to the monitor station where it is used to actuate an identical set of resistors to reproduce the input resistance value.

5 Claims, 12 Drawing Figures

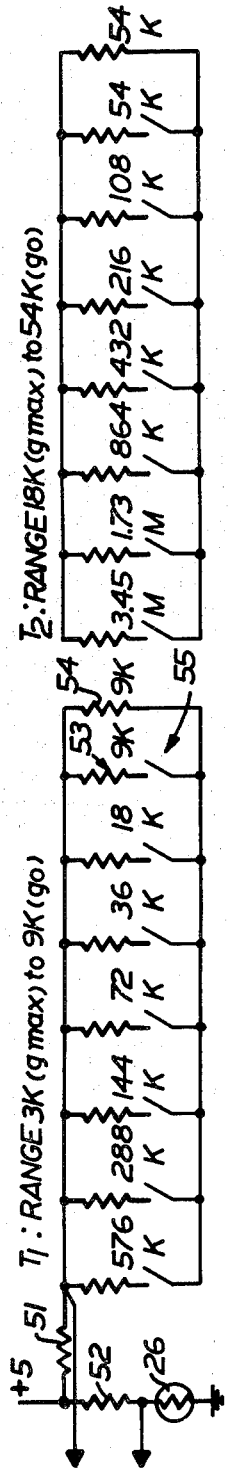
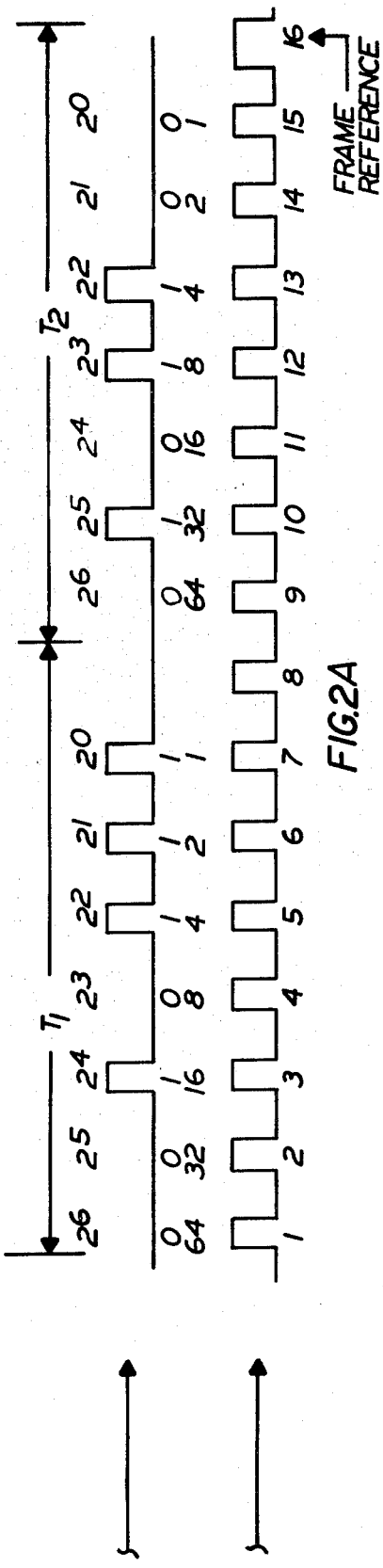
FIG.2A
FIG.8

FIG. 4 PRESSURE CHANNELS, TRANSMIT

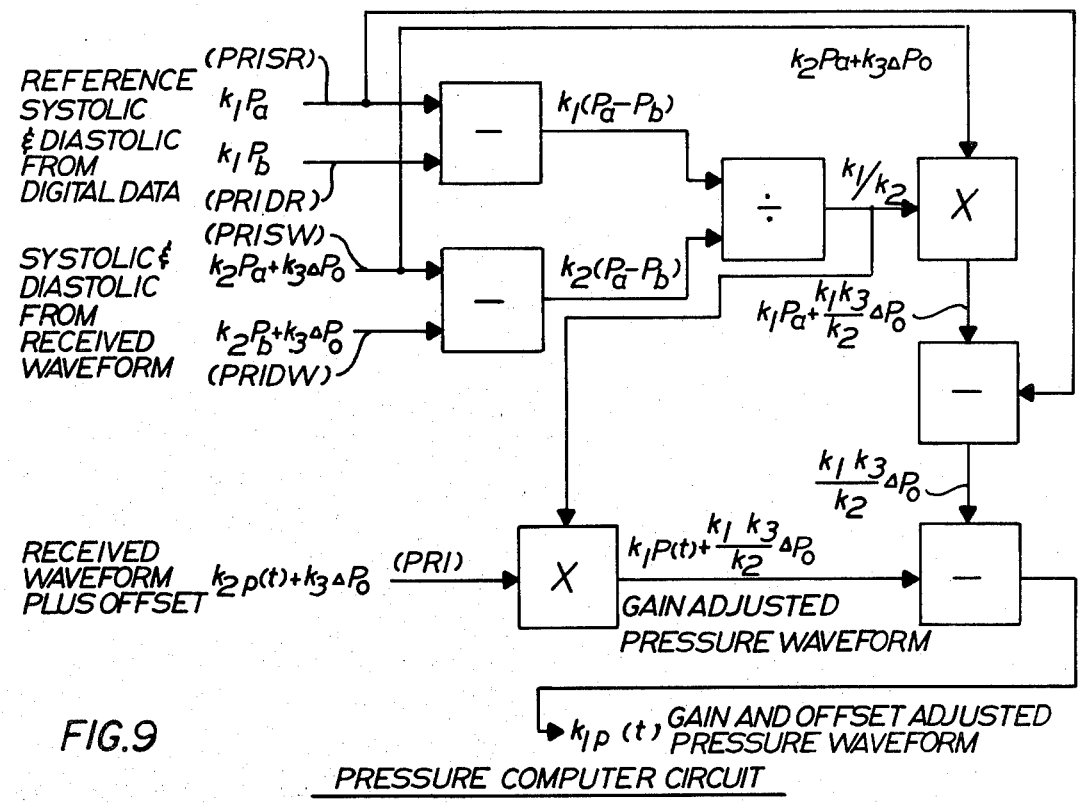
FIG. 9 PRESSURE COMPUTER CIRCUIT
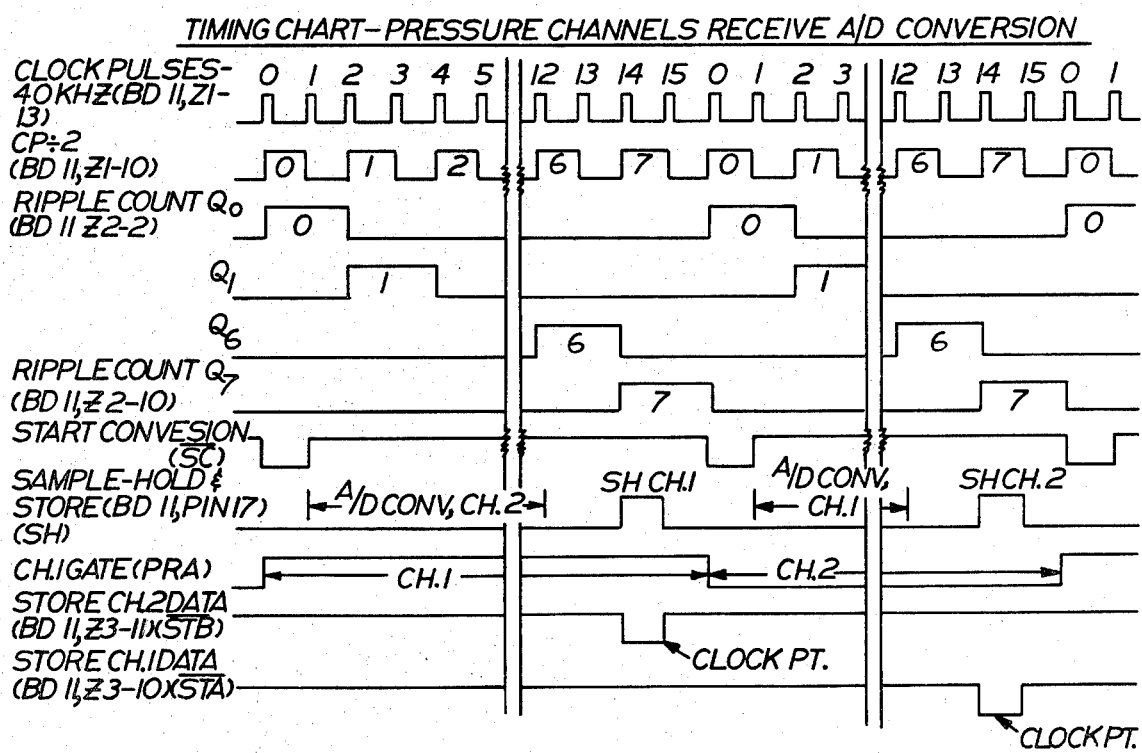
FIG. 11

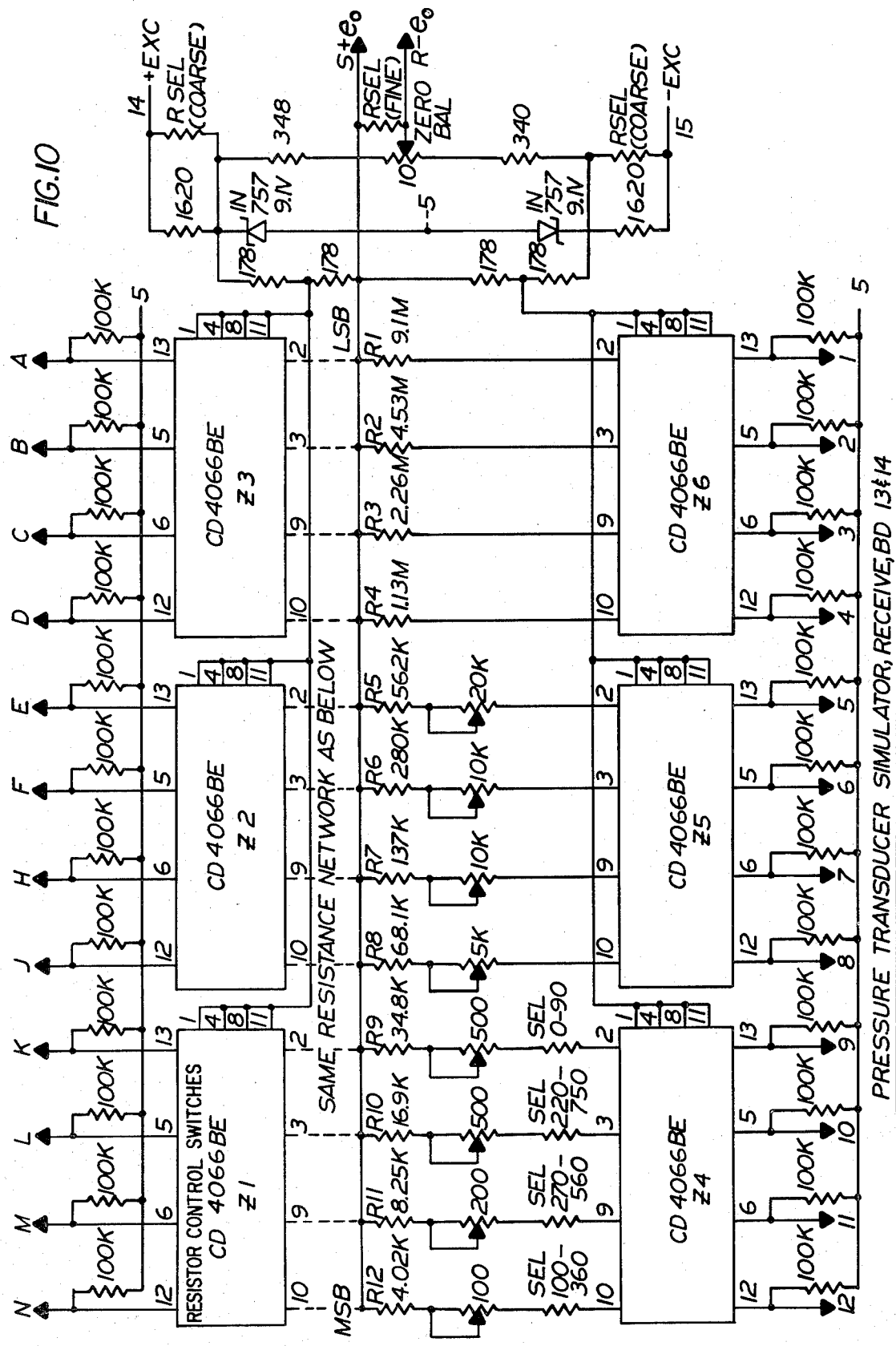

TELEMETERING SYSTEM FOR OPERATING ROOM AND THE LIKE

This is a division of application Ser. No. 956,593, filed Nov. 1, 1978.

BACKGROUND OF THE INVENTION

This invention relates to transmission of data and in particular to the telemetering of biomedical data of a patient to a monitor for display.

Telemetry systems are now being widely used clinically to monitor post surgical patients and cardiac patients. Typical commercial systems are single channel and are used for ECG monitoring. Some experimental multichannel systems have been reported in literature for use in surgical monitoring and intensive care monitoring. These systems propose a voltage controlled oscillator for each channel with an FM modulated carrier which is demultiplexed at the receiving end utilizing band pass filters and frequency discriminators. Other systems have used pulse width modulation or other conventional modulation formats, and several multichannel systems are now available commercially. Also, systems providing a plurality of data channels for direct connection between a plurality of transducers and/or sensors and a monitor are available commercially.

It is an object of the present invention to provide a new and improved telemetering system especially suited for use with a medical patient and providing a plurality of data channels. A further object is to provide such a system which can be interposed between the conventional transducers and the conventional monitor without requiring changes or adjustments of either. A further object is to provide a telemetering system for a resistance value with the output simulating the resistance at the input so that the monitor operates the same with direct transducer connection and telemetering system connection as input.

It is a particular object of the invention to provide a telemetering system for transmitting a pressure wave such as a recurring pulse pressure wave, providing for transmission of the waveform and values of the peak and trough corresponding to the systolic and diastolic pressures, respectively. An additional object is to provide a telemetering system for transmission of a temperature value with high resolution and high accuracy and low drift so that introduction of a telemetering system does not introduce any additional error in the overall measurement.

These and other objects, advantages, features and results will more fully appear in the course of the following description.

SUMMARY OF THE INVENTION

The inventor includes method and apparatus for transmission of data, particularly resistance values. The system of the invention has as an input the resistance of a conventional transducer end provides as output a resistance identical to the transducer resistance.

The waveform telemetering system includes means for providing an output voltage varying as a function of the transducer output, means for detecting peak and trough values and producing signals corresponding to these values, means for connecting the output voltage and the peak and trough values to the transmission link, means for detecting peak and trough values of the received output voltage, means for comparing transmitted and received peak and trough values and changing the peak and trough of the transmitted output voltage so that the resultant voltage corresponds to the initial voltage, and means for converting this resultant voltage to a varying resistance.

The telemetering system for transmission of a resistance, such as a temperature sensor resistance, includes a bridge with the temperature sensor connected as one arm and a control resistor connected as another arm. Means are provided for varying the control resistor, preferably a counter which selectively drives switches in a resistor bank, to obtain a balance of the bridge, at which time a signal, preferably a digital code, based on the count state of the counter and corresponding to the resistance introduced into the bridge is transmitted on the transmission link to the receiver. At the receiver a corresponding variable resistance is changed as determined by the transmitted code to produce a resistance value corresponding to the sensor resistance, which resistance value is connected to the monitor.

Both method and apparatus for telemetering are included. While the preferred embodiments provide for transmission of pressure and temperature data, it will be realized that the invention is not so limited and that the transmission of resistance values representing other parameters is included in the invention.

BRIEF DESCRIPTION OF THE DRAWINGS

FIGS. 2 and 2A are a block diagram for the temperature channel of the system of FIG. 1;

FIG. 8 is a truth table for the pressure channels receive portion of FIG. 5;

FIG. 9 is a block diagram illustrating the pressure computer circuit of FIG. 5;

FIG. 10 is a schematic diagram of the pressure transducer simulator of FIG. 5; and FIG. 11 is a timing chart for the receiving pressure channels analog to digital conversion.

DESCRIPTION OF THE PREFERRED EMBODIMENTS

The telemetering system of the present invention was designed to make possible accurate, reliable radio telemetry of a sufficient number of physiological parameters to enable a surgical patient to be monitored adequately with no electrically-wired connections to the patient-monitor device.

The parameters chosen were as follows:
1. ECG (five lead)
2. Peripheral Pulse (using photo-optical sensor)
3. Temperature (one channel, expandable to two channels)
4. Pressure (two channels)

The major goals of the system were:

1. Employ standard transducers with few or no adjustments required by the user in addition to those normally performed using a conventional patient monitoring system,
2. Provide redundancy by allowing all transducers in use to be interconnected directly, with little or no readjustment, to either the transmitter or to the patient monitor,
3. Require no special display device other than a conventional patient monitor system,
4. Provide a multiplexed data format suitable for recording all parameters on one track of a conventional high quality stereo or monaural cassette recorder,
5. Conform to all applicable current patient safety regulations, and
6. Provide rechargable battery power for the transmitter unit sufficient to enable at least eight hours of continuous monitoring before recharging is necessary.

Figure 1:
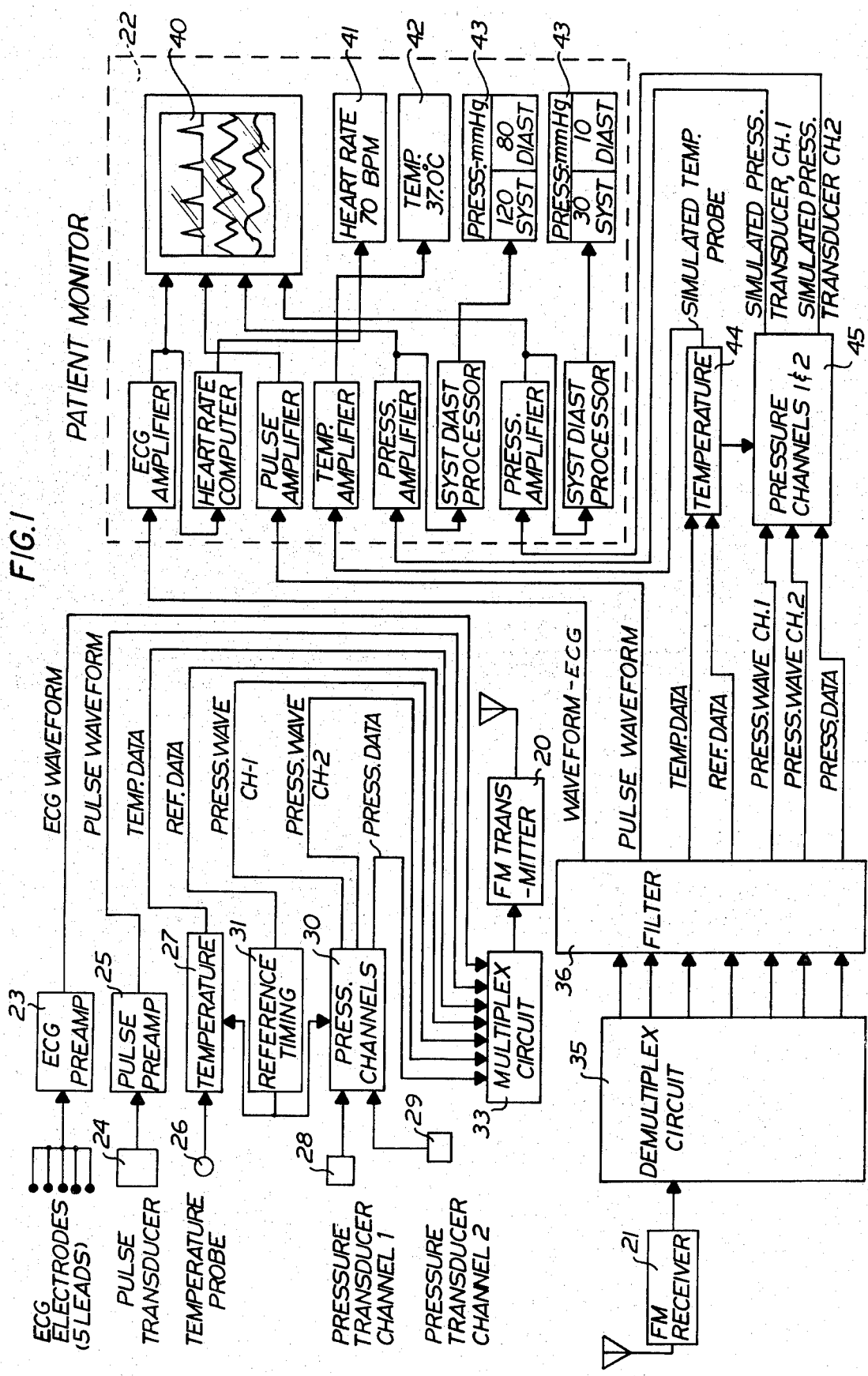
FIG. 1 is a block diagram of a telemetering system incorporating the presently preferred embodiment of the invention.

The overall system is illustrated in FIG. 1. A conventional FM transmitter 20 and a conventional FM receiver 21 are used as the transmission link between the transducers and other pick-ups on the patient and the patient monitor 22. Of course, other transmission links may be utilized if desired.

Leads from conventional ECG electrodes connected to an ECG preamplifier 23. A conventional pulse transducer 24 is connected to a pulse preamplifier 25. One or more conventional temperature probes 26 are connected to a temperature unit 27. Conventional pressure transducers 28, 29 are connected to a pressure unit 30. A timing unit 31 provides timing reference signals to the temperature unit 27 and pressure unit 30.

The preamplifiers 23, 25, the temperature unit 27, the pressure unit 30, and the timing unit 31 provide seven outputs to a multiplex circuit 33. The multiplex circuit may be a conventional multiplexer which provides the information signal to the transmitter 20. Alternatively, the seven outputs may be transmitted separately without multiplexing.

The signal from the receiver 21 is connected to a demultiplex circuit 35 which produces seven outputs corresponding to the seven outputs connected to the multiplex circuit 33. The outputs from the demultiplex circuit 35 pass through a conventional filter 36.

The patient monitor 22 is a standard device and includes an ECG amplifier, a heart rate computer, a pulse amplifier, a temperature amplifier, two pressure amplifiers, and two systolic/diastolic processors. The output of the ECG amplifier is connected to a multitrace cathode ray tube 40 and to the heart rate computer. The output of the pulse amplifier and both pressure amplifiers are also connected to the tube 40. The output of the heart rate computer is displayed at a digital display 41. The output of the temperature amplifier is displayed at another digital display 42. The output of each pressure amplifier is connected to the corresponding systolic/diastolic processor, with the output of each processor connected to a display 43 which shows systolic and diastolic pressures for the particular channel.

The ECG waveform from the filter 36 is connected directly to the ECG amplifier of the patient monitor. Similarly the pulse waveform from the filter is connected directly to the pulse amplifier of the patient monitor. The temperature data and the reference data from the filter are connected to a temperature unit 44. The channel 1 and channel 2 pressure waves and the pressure data from the filter are connected to a pressure unit 45. The output of the temperature unit 44 is connected to the temperature amplifier of the patient monitor. The outputs for the two channels from the pressure unit 45 are connected to the corresponding pressure amplifiers of the patient monitor. The temperature and pressure units will be described in greater detail hereinbelow.

The system functions to connect the ECG electrodes, the pulse and pressure transducers, and the temperature probes to the patient monitor through a transmission link in a manner such that the inputs presented to the patient monitor correspond to that which would be presented if the electrodes, transducers, and probes were directly connected to the patient monitor in the conventional manner. This permits remote positioning of the patient monitor from the patient and this may be accomplished without requiring any direct wire connections therebetween. The transducer and transmitter portion may be battery powered and quite small, permitting installation in a small volume on a patient trolley and permitting movement of the patient trolley without concern for trailing wires. The wire connections from the receiver section to the patient monitor are directly interchangeable with the wire connections from the electrodes, transducers and probes. No adjustments or calibration are needed other than the normal patient monitor adjustments since all outputs from the receiver unit are identical to the corresponding electrode, transducer and probe outputs. Thus, in the event of failure of the telemetry system, any or all transducers may be immediately connected directly into the patient monitor system with no necessity for recalibration.

ECG & Pulse Channels

The ECG preamplifier 23 is of conventional design and uses a five-lead input cable. The amplifier is designed primarily to measure the V-5 lead. A three-lead cable can be used to measure leads I, II, or III by use of a suitable adapter. The amplified output of the ECG amplifier is connected to the input of the multiplex circuit 33, to be multiplexed with other signals and transmitted.

The pulse transducer preamplifier 25 provides regulated DC excitation to the light source of the transducer 24 and amplification of the phototransistor output which is then routed to the multiplex circuit 33.

Transmit/Multiplex Functions

Multiplexing at unit 33, FIG. 1, is performed at a 2 KHz rate using an eight-channel pulse-position format, with one channel used only for synchronization. The final pulse-position modulated format is derived from a basic pulse-width modulated waveform. The pulse position format was found to be more desirable for FM transmission with commercially available entertainment-type transmitters and receivers because of the elimination of most of the low frequency components present in the pulse width modulation format.

The pulse-position modulation information is applied to a commercial FM microphone transmitter 20 operating at approximately 88 mHz, and at a maximum input power of 100 mw.

Demultiplex Circuit

The function of the demultiplex circuit 35 is to separate each of the seven channels of data from the pulse-position modulated waveform provided at the output of the FM receiver 21.

In the system disclosed, the pulse position modulation is first applied to an automatic gain control which provides approximately 4 vpp out for input signals ranging from 20 mv pp to 6 vpp. The modulation is then applied to a squaring circuit with hysteresis, which ignores baseline noise on the waveforms and converts the modulation to a pulse-width modulated format. Further squaring is provided by a comparator. Conversion of pulse-widths to amplitudes is accomplished with a conventional operational amplifier-integrator. Two identical sample-and-hold amplifiers are used to sample alternate channels so that cross-talk between channels is minimized, and maximum efficiency of data recovery is achieved.

Temperature Channel

Temperature information ordinarily is transmitted as a voltage or frequency proportional to temperature. This mode of operation requires careful calibration of the circuitry at the transmitter unit. In order to obtain drift free measurement in the system of the present invention, a precision resistance measuring bridge and a digital circuit which encodes the resistance value for transmission to the receiving circuit is utilized. The receiving circuit produces an electrical resistance identical to the temperature sensor resistance for presentation to a conventional monitor which may measure, record and/or display the temperature. This permits transmission of temperature information with no more drift than if the temperature sensor or probe was connected directly to the monitor. Resolution in the measuring system is a function of the number of digital increments utilized and in the embodiment illustrated herein, 128 increments are used providing ±0.1° C. resolution.

Measurement of temperature using a thermistor probe is conventionally done by developing a voltage-proportional-to-temperature using a bridge amplifier, then developing a numerical readout based upon the voltage obtained. The system of the present invention differs from the conventional system in that there is no need to duplicate the amplifier and display system at the patient, and that by utilizing the conventional patient monitor for display, user convenience is greatly enhanced. The output from the temperature unit 44 is electrically identical to the output of the temperature probe 26 permitting use of the conventional patient monitor 22 for display of telemetered temperature information.

Figure 2:
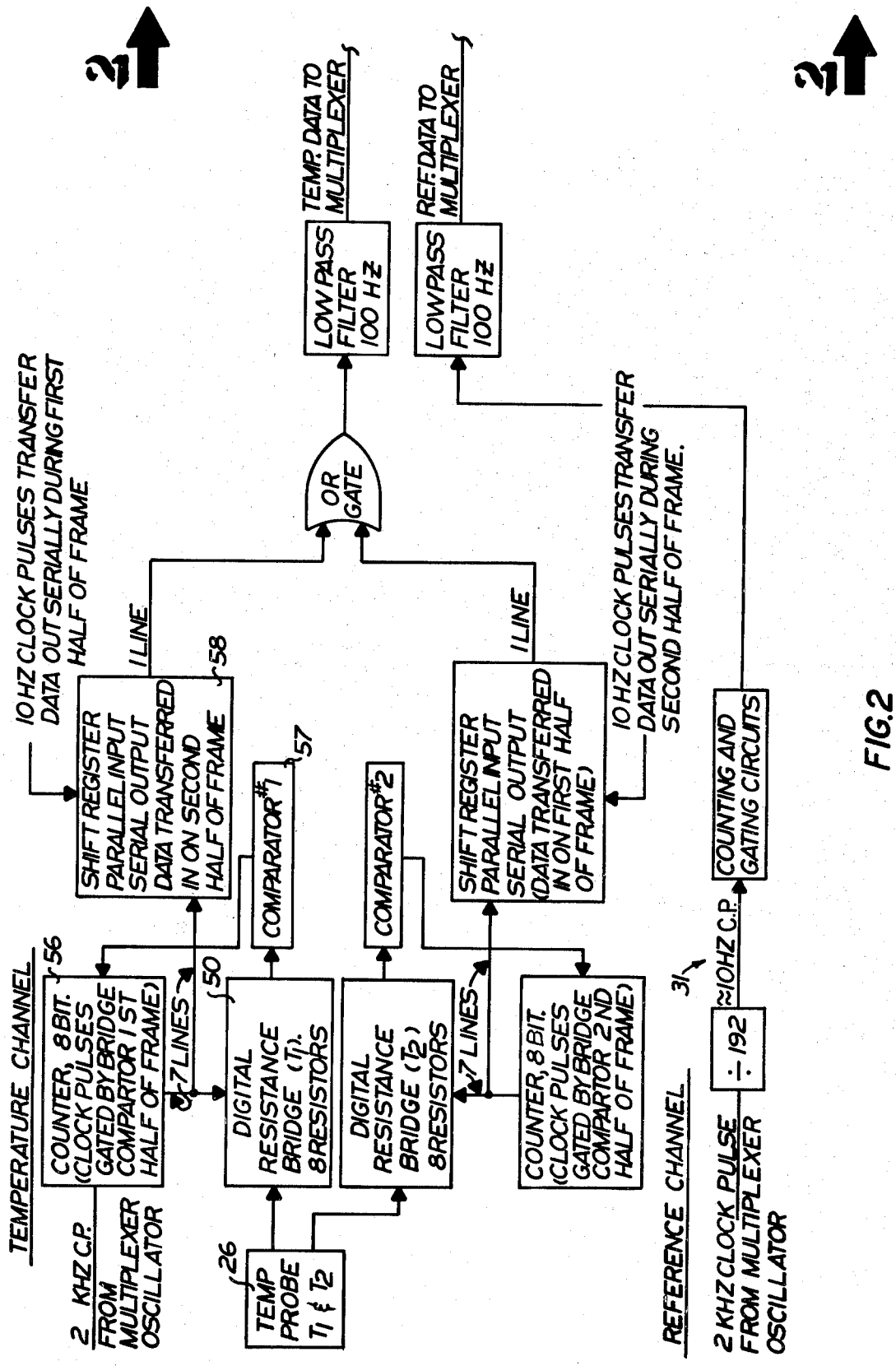
Figure 3:
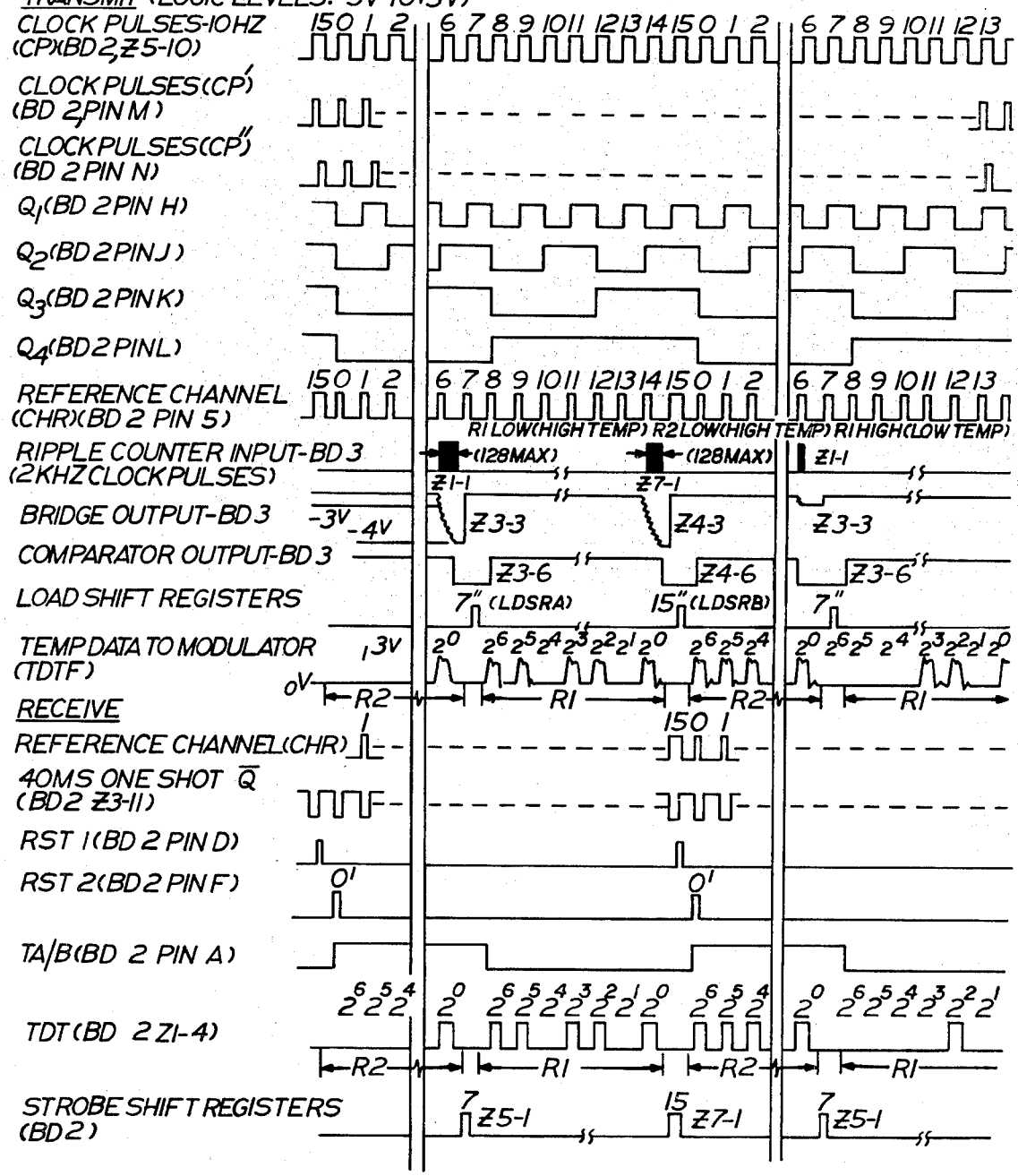
FIG. 3 is a timing chart for the temperature channel of FIG. 2.

A preferred embodiment of the temperature unit 27 is shown in FIGS. 2 and 2A, and timing of waveforms used for temperature measurement is shown in FIG. 3. Thermistor temperature probes often contain two separate thermistors, so that two separate resistance measurements must be made for each temperature measurement. Each thermistor 26 is connected into a bridge circuit 50 containing two precision resistors 51, 52 and seven electronically switchable resistors 53, of value R, 2R, etc., in parallel with a fixed resistor 54. The fixed resistor is equal to the largest expected thermistor resistance (corresponding to the minimum temperature measurement desired). The seven switchable resistors are switched in different combinations to obtain $2^7$ discrete resistance values, or 128 different values. With all seven resistors in parallel with the fixed resistor, the total resistance is equal to the lowest expected resistance of the thermistor (corresponding to the highest temperature desired). Over a temperature range of 15° C. to 40° C., 128 discrete steps of resistance variations provide a temperature resolution of approximately 0.2° C., or ±0.1° C.

The seven resistors 53 are switched by switches 55 controlled by a binary counter circuit 56 until the comparator 57 senses that the bridge is close to balance. The binary value of resistances in the circuit at that instant in time is transferred in seven-bit parallel binary words into a storage register 58. The bits are then clocked out of the register 58 serially by 10 Hz clock pulses to be multiplexed onto one data control, and the 10 Hz reference pulses are routed to another data channel of the transmission link.

Data words for the two resistance values of the two probes are alternately clocked onto the data line to form a 16-bit word consisting of 14 data bits, with bits 15 and 8 unused, since synchronization and storage occur during the time of the two unused data bits.

Reference clock pulses and other timing waveforms are generated in a conventional manner. The reference channel contains 15 narrow pulses (bits $01 \propto 14$) and one wide pulse (bit 15) which is used for frame synchronization. A new temperature measurement is made every frame, or approximately once per 1.6 seconds. Typical thermistor resistance calculations are shown below.

The resistance R of the probe thermistor is represented by the following relation:

$1/R = (\Sigma 2^n) g + g_o$, where $g_o = 1/R_{max}$ $\Lambda g = (1/R_{max} - g_o)/2^n$ n = number of resistors to be switched N = data bit numbers For the temperature $T_1$ in FIG. 2A with data code 0010111 and resistance values shown $R_1 = 1/(23\Lambda g + g_o)$ $g_o = 1/9k = 1.1111 \times 10^{-4}$ $\Lambda g = (3.3333 \times 10^{-4} - 1.1111 \times 10^{-1})\Lambda 28 = 1.7360 \times 10^{-6}$ $R_1 = 1/(23 \times 1.7360 \times 10^{-6} + 1.1111 \times 10^{-4}) = 6620.76$ ohms Similarly for $T_2$ in FIG. 2A with code 0101100

$R_2 = 1/(44\Lambda g + g_o)$ $g_o = 1/54 \ k = 1.8518 \times 10^{-5}$ $\Lambda g = (5.5555 \times 10^{-5} - 1.8518 \times 10^{-5})/128 = 2.8934 \times 10^{-7}$ $R_2 = 1/(44 \times 2.8934 \times 10^{-7} + 1.8518 \times 10^{-5}) = 32001.1$ ohms Temperature Decoding The temperature unit 44 for received signals contains identical swtiched-resistor networks to those in the temperature unit 27, providing a resistance value to the temperature amplifier of the monitor 22.

Temperature data is received in a format containing two seven-bit binary words per frame, representing the two resistance values necessary to simulate the two temperature probe resistances for the given temperature being measured. Each binary word is serially loaded into a shift register and then read out in parallel and connected to seven CMOS switches (two type 4066 integrated circuits) which connect the proper resistances in parallel to reproduce the two temperature probe resistances measured by the transmitter unit. These resistances are connected to the temperature probe input of the patient monitor so that the temperature may be determined and displayed.

Pressure Channels, Transmit

Figure 4:
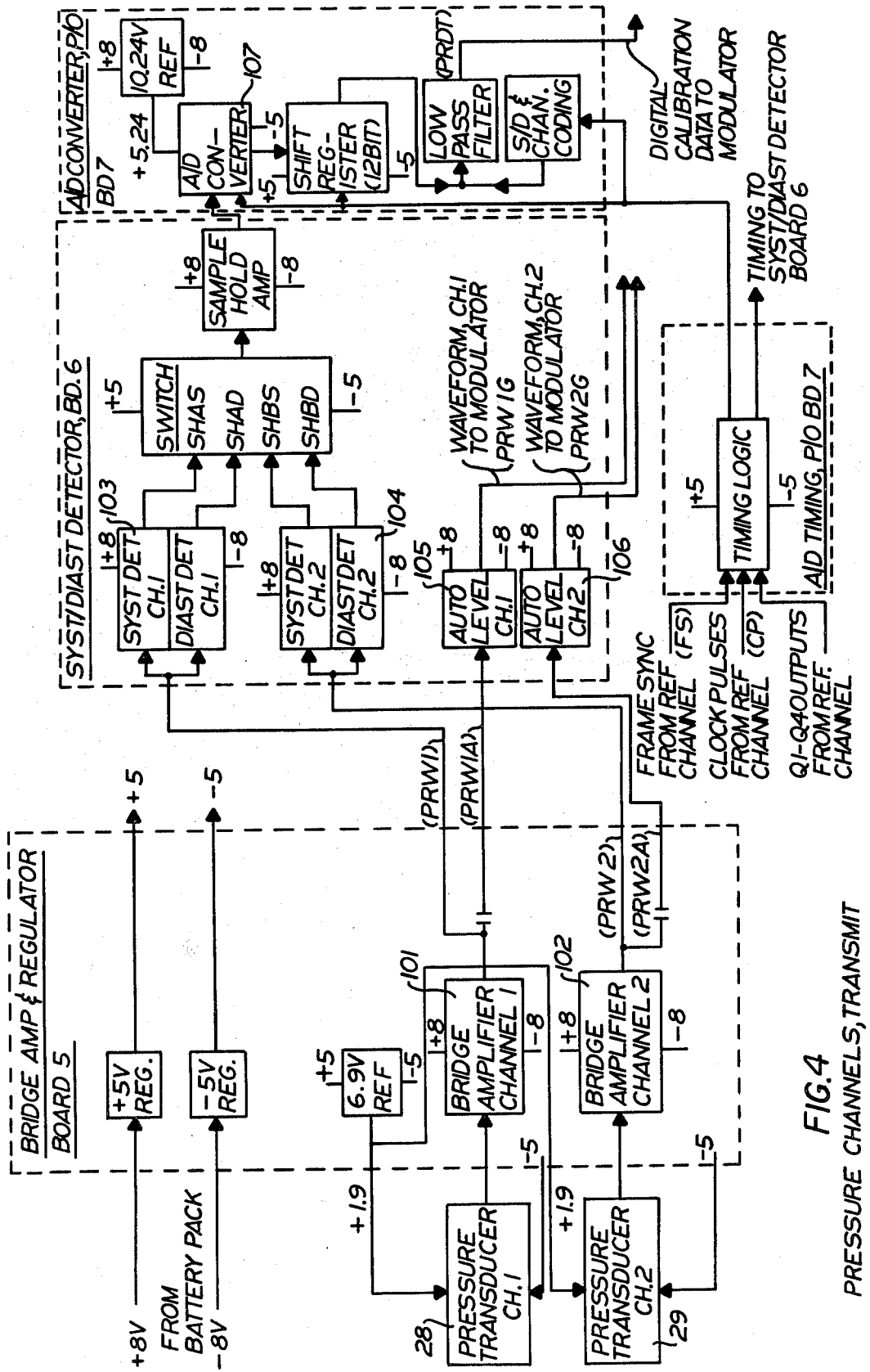
FIG. 4 is a block diagram illustrating the transmitter portion of the pressure channels of the system of FIG. 1.
Figure 6:
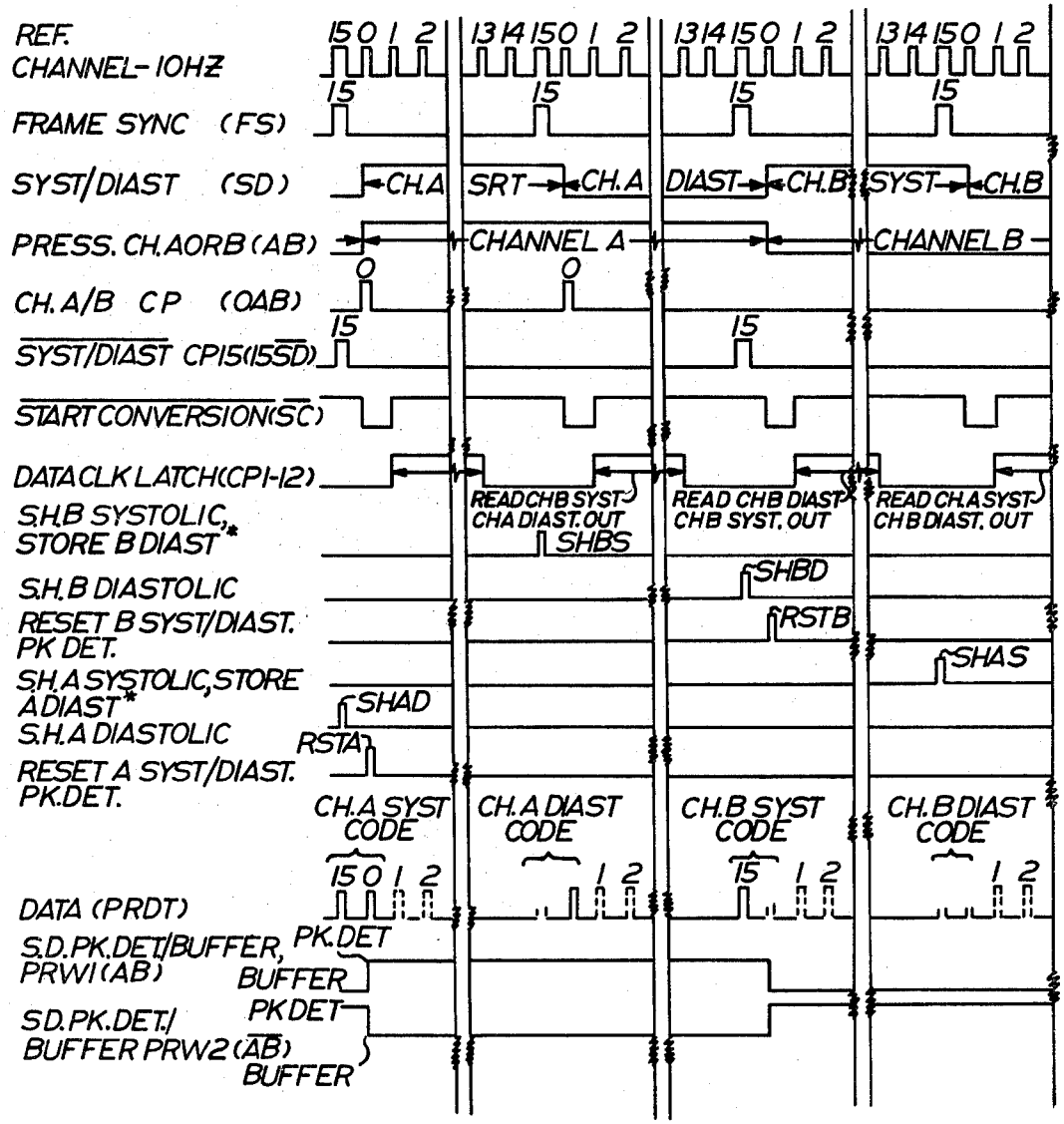
FIG. 6 is a timing chart for the transmit pressure channels.

The pressure unit 30 of the transmit section is shown in greater detail in FIG. 4 and the operation is shown in the timing chart of FIG. 6.

The pressure unit 30 includes two pressure transducer bridge amplifiers 101, 102 with common bridge excitation supply, dual-channel systolic/diastolic detectors 103, 104, dual automatic level control 105, 106 for pressure-wave amplitude control to enhance signal-to-noise at low pressures, and an analog-to-digital converter 107 with associated data registers for converting parallel digital pressure reference and calibration data into serial data suitable for multiplexing and transmitting.

Two data channels are required to transmit complete information for one pressure channel while only three data channels are required to transmit complete information for two pressure channels. One channel is used for alternately transmitting discrete digital values of systolic and diastolic pressure for each of the two pressure waveforms and the remaining two data channels are used for transmitting the two pressure waveforms. The digital data is in the form of four 16-bit words which are transmitted serially. Each 16-bit word contains 12 data bits, two identification bits, and two unused bits. Preferably analog waveform information is first amplitude adjusted by the automatic level units 105, 106 to provide better signal-to-noise ratio; no absolute pressure waveform amplitude or offset is retained since this is added at the receive section from data received from the pressure reference channel.

Pressure Bridge Amplifier

The two pressure bridge amplifiers 101, 102 are of conventional design and preferably employ extremely low-drift integrated circuit amplifiers combined with a well-regulated excitation-voltage supply so that drifts due to non-transducer related sources are kept to a minimum, typically much less than 1 mm Hg. Balance indicators are provided for each channel so that transducers with adjustable zero-balance controls can be conveniently balanced. No amplifier balance or sensitivity adjustments are needed since calibration factors and any residual offsets are taken care of by the pressure module of the patient monitor 22 just as if the transducers were connected directly into it.

Systolic/Diastolic Detector

The systolic and diastolic detector circuits 103, 104 are located on board 6, FIG. 4. The board contains two identical systolic detector/memory circuits and two identical diastolic detector/memory circuits as well as two identical auto level control circuits 105, 106.

The systolic detector/memory circuits and diastolic detector/memory circuits are identical in function except for the polarity of the feedback to the peak detector switch. Peak detection and memory are performed alternately by providing the proper logic levels so that a CA 3130A integrated circuit is first connected as a comparator, causing the switch to sample the incoming waveform, then as a conventional unity-gain high input-impedance buffer to enable reading of the voltage stored on the memory capacitor, which represents the previously determined systolic or diastolic value. After the systolic or diastolic value is read, a reset pulse causes the memory capacitor to be charged to a voltge equal to the voltage of the pressure waveform at the instant of the reset pulse, so that a new value of systolic or diastolic pressure can then be determined. A truth-table of circuit functions of the systolic/diastolic/memory circuits is shown in FIG. 8.

Automatic Level Control

The automatic level control circuits, 105, 106 are located on board 6, FIG. 4. These circuits adjust the amplitudes of the AC-coupled pressure waveform according to the value of pulse-pressure. Discrete pulse pressure values for each waveform are computed from values obtained by the systolic/diastolic detector circuits. The pulse pressure value is then stored and applied to a field effect transistor, operating in the variable resistance mode and connected into an attenuator circuit, so that small amplitude pressure waveforms are caused to be amplified more than large amplitude pressure waveforms.

Analog to Digital Conversion

The analog to digital converter 107 on board 7, FIG. 4, generates additional timing waveforms required for the pressure channels as well as performing A-to-D conversion of the systolic and diastolic information. FIG. 6, the Timing Chart, Pressure Channels, Transmit, shows waveform details. Preferably, a precision monolithic integrated circuit 12-bit analog-to-digital converter is used in conjunction with a precision voltage reference so that digital pressure reference information transmitted to the receiver/demultiplexer can be used to reconstruct the original pressure information within the required overall accuracy specifications.

Pressure Channels, Receive

Figure 5:
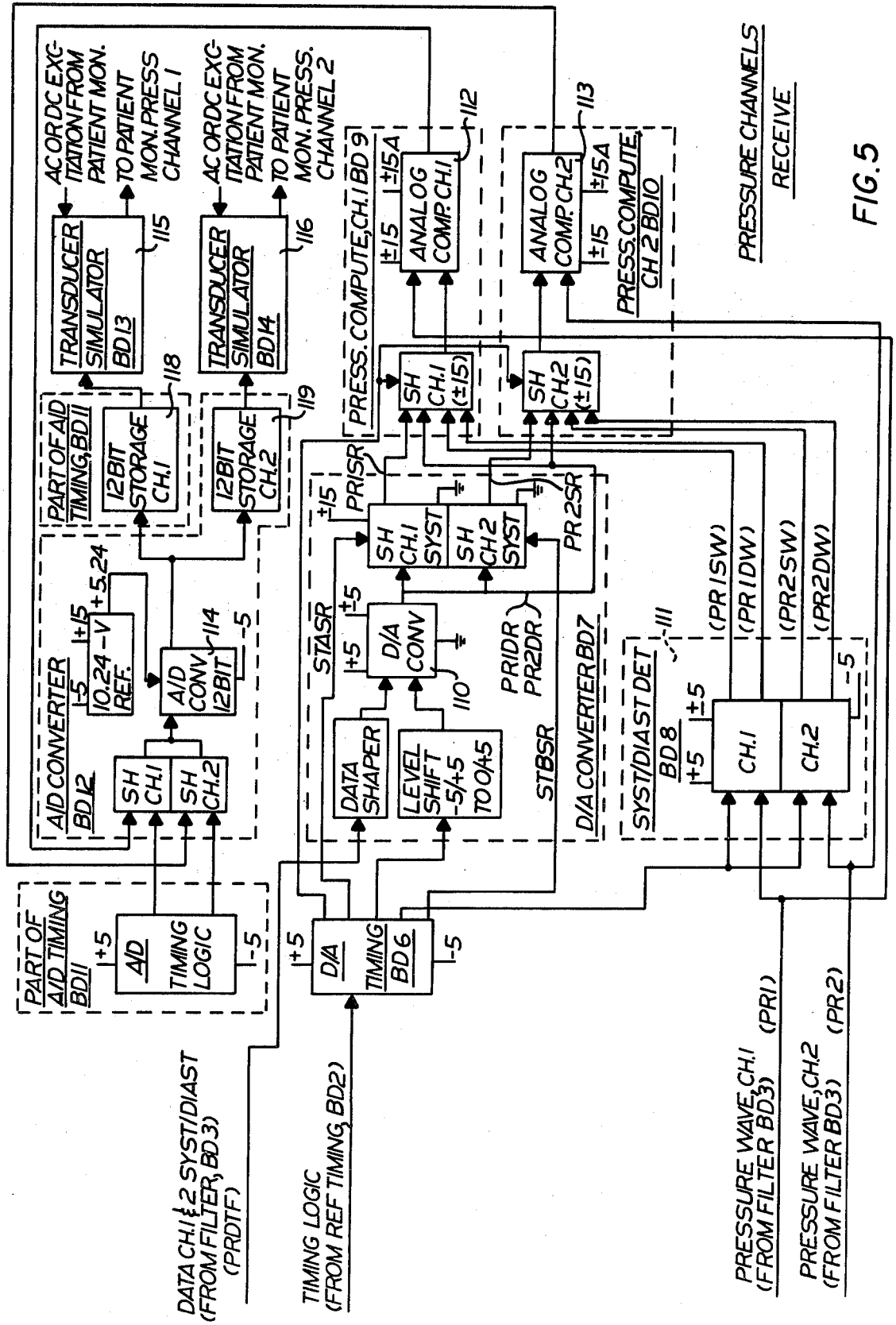
FIG. 5 is a block diagram illustrating the receiving portion of the pressure channels of the system of FIG. 1.
Figure 7:
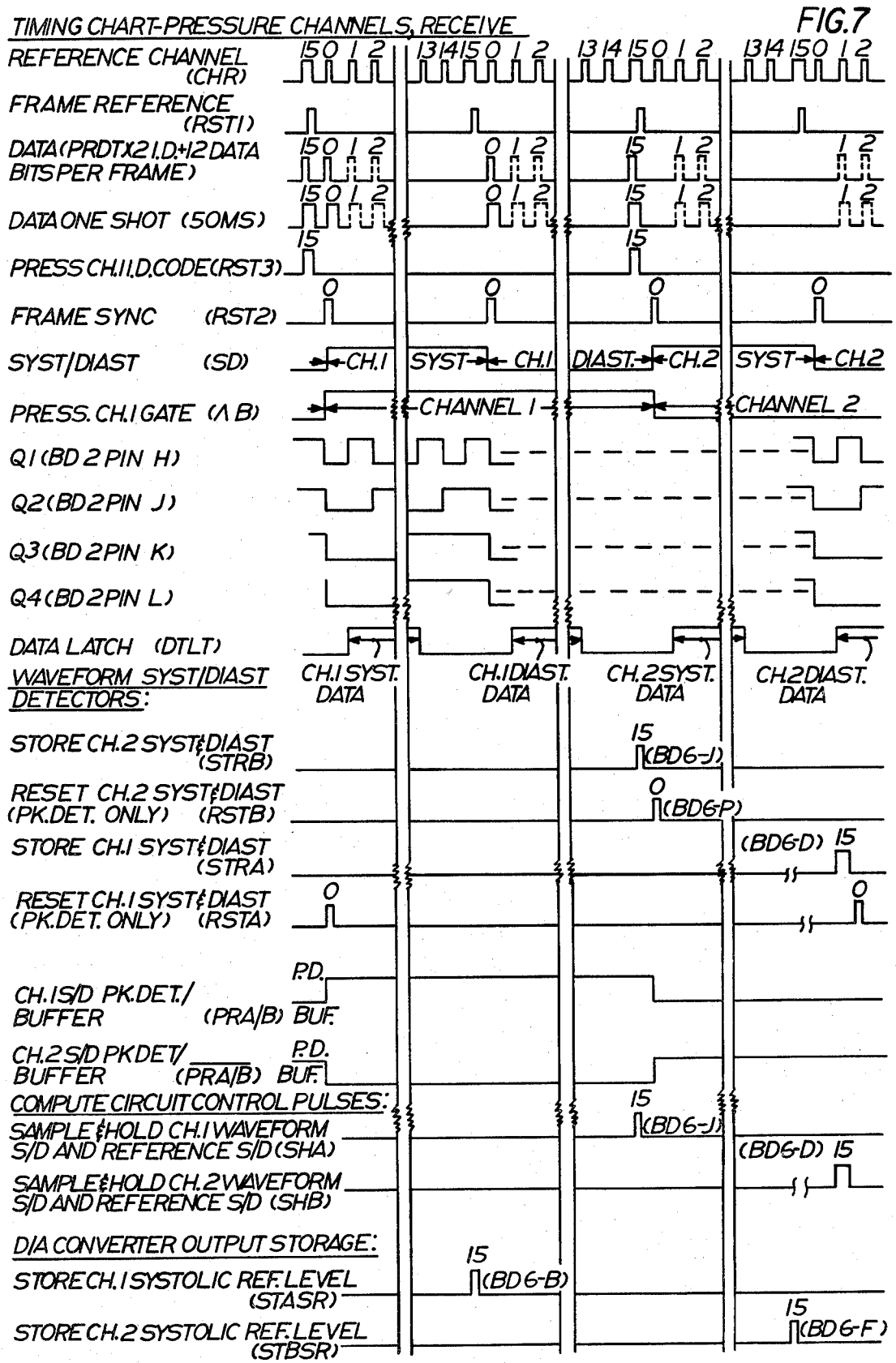
FIG. 7 is a timing chart for the receive pressure channels.

The pressure unit 45 of the receive section of FIG. 1 is shown in greater detail in FIG. 5 and the operation is shown in the timing chart of FIG. 7.

The pressure unit 45 includes a digital-to-analog converter 110 for converting digitally-encoded values of systolic and diastolic pressures to analog voltages, a dual-channel systolic/diastolic detector/memory circuit 111 for measuring and storing systolic and diastolic values of the two received pressure waveforms, two analog computing circuits 112, 113 for continually adjusting pressure waveform amplitude and offset, an analog-to-digital converter 114 which provides digital encoding of the two calibrated pressure waveforms, and two pressure transducer simulator circuits 115, 116 which convert the A-to-D digitally encoded waveform data into resistance changes which can be interpreted by the patient monitor pressure modules as pressure transducer signals.

The digital converters (A-to-D and D-to-A) are standard monolithic integrated circuits and their associated timing circuitry is of conventional design.

The function of the receive pressure measuring circuitry is to use the reference channel digital information to effect accurate amplitude and offset correction of two pressure waveforms and then cause resistance changes proportional to each waveform to be presented to the respective pressure transducer inputs of a conventional patient monitor 22. The principal difference between the telemetered pressure signals and direct-coupled pressure signals is that a periodic amplitude and offset adjustment is made upon the waveforms of the telemetered signals. Normally only a negligible change in waveform gain and offset will occur between the instant the reference systolic and diastolic values are measured by the transmit unit until the instant of waveform adjustment at the receive unit (approximately eight to ten seconds). This time lag is necessary because of information-bandwidth constraints in the specific system disclosed, and was the result of a tradeoff between the number of channels desired and accuracy of pressure measurement required. Some advantages of the method are, (1) accuracy of pressure readings (after initial stabilization time) and (2) attenuation of cross-talk noise on the pressure waveform (due to increase in gain at the transmitter and readjustment of gain at the receiver).

Pressure Computer Circuits

The pressure computer circuits 112, 113 are analog computing circuits composed of operational amplifiers and analog multipliers which together perform gain adjustment and offset adjustment of the received pressure waveforms. This is done by utilizing digitally encoded systolic and diastolic pressures measured by the pressure measuring circuits in the transmitter unit as reference values to which the received waveforms may be compared and adjusted accordingly. One computer circuit is shown in greater detail in FIG. 9, where $P_a$ = Systolic pressure + 50 mmHg
$P_b$ = Diastolic pressure + 50 mmHg
$\Delta P_o$ = Offset pressure
$k_1$ = Standard gain constant of pressure signal = 20 mv/mmHg
$k_2$ = Gain constant of received pressure waveform, V/mmHg
$k_3$ = Gain constant of zero offset of received signal, V/mmHg
p(t) = Received pressure waveform (Time varying pressure)

The two types of operations which are performed are gain adjustment and offset adjustment. Gain adjustment is performed by subtracting the diastolic reference value $k_1 P_b$, from the systolic reference value, $k_1 P_a$, and dividing this value into the value obtained by subtracting the received waveform diastolic-plus-offset value, $k_2 P_b + k_3 \Delta P_o$, from the received waveform systolic-plus-offset value, $k_2 P_a + k_3 \Delta P_o$, to obtain a gain ratio $k_1/k_2$, which is then continuously multiplied times the received pressure waveform, $k_2 p(t) + k_3 \Delta P_o$, to adjust its gain. The amplitude adjusted waveform plus offset, then, can be represented by the term, $k_1 p(t) + (k_1 k_3/k_2) \Delta P_o$.

Zero offset correction is performed by multiplying the received waveform systolic pressure-plus offset, $k_2 P_a + k_3 \Delta P_o$, by the previously obtained gain ratio, $k_1/k_2$, subtracting the reference systolic value, $k_1 P_a$, to obtain the offset error, $(k_1 k_3/k_2) \Delta P_o$, and then continuously subtracting the offset error from the gain-adjusted waveform-plus-offset, $k_1 p(t) + (k_1 l_3/k_2) \Delta P_o$, to obtain the final gain and offset adjusted waveform $k_1 p(t)$.

In the event that the apparent systolic minus diastolic pressure of the received waveform (pulse-pressure) is below about 10 mmHg, the gain adjustment circuitry is inactivated and only the offset circuit remains in effect. However, 10 mmHg measured from the received waveform corresponds to an actual value of perhaps one or two mmHg due to the increased gain applied to the pressure waveforms at the transmitter by the automatic level control circuitry.

Pressure Transducer Simulator and A/D Conversion

One pressure transducer simulator unit 115 is shown in greater detail in FIG. 10 and operation of the converter 114 and units 115, 116 as shown in the timing chart of FIG. 11.

The simulator circuit of FIG. 10 is basically a conventional four-arm resistance bridge with two digitally-controllable variable arms. AC or DC excitation is applied externally by the respective pressure module of the patient monitor 22. Bridge arm resistance changes are effected by 12 precision resistors R12-R1 of ratio R, 2R, etc., in parallel with each of two arms of the bridge, and which are caused to be switched in and out of the circuit in a binary-coded fashion. A binary code corresponding to pressure measured at a given instant in time is applied to the twelve switches Z1, Z2, Z3 which control the resistors in parallel with one arm of the bridge, while at the same instant, the binary compliment of that code is applied to the twelve switches Z4, Z5, Z6 controlling the resistors in parallel with the opposite arm of the bridge. Bridge linearity is thus preserved, since a significant non-linear effect would result if only one arm of the bridge were varied.

The twelve bit binary code is generated by the A to D converter 114, which alternately samples the two gain and offset adjusted pressure waveforms. Each channel is sampled approximately 1250 times per second. The twelve-bit binary words representing instantaneous pressure mesurements are stored in two 12-bit parallel-in/parallel-out shift registers 118, 119, one register for each pressure channel. Shift register outputs are connected directly to one bank of bridge-arm resistor-control switches, and the complement (inverse) of these outputs are connected to the opposite bank of bridge arm resistor control switches.

The upper frequency response limit of each pressure channel corresponds to one-half the sample rate, or 625 Hz. The component presently used for the A/D converter 114 has a maximum possible resolution of one part in $2^{12}$, but is guaranteed for only one part in $2^{10}$. Therefore guaranteed full scale resolution is one part in $2^{10}$ or one part in 1024. The full scale range of pressure of the A/D converter is 500 mmHg, so that guaranteed resolution is (500/1024), or better than $\frac{1}{2}$ mmHg.

I claim:
1. A telemetering system for transmitting temperature information between a temperature probe and a temperature monitor, said probe including a resistor with the resistance thereof varying as a function of its temperature, including in combination:
a transmission link having transmitter and receiver;
a bridge circuit including means for connecting said probe resistor in an arm of said bridge circuit;
a plurality of resistors connected as a first resistor bank;
first switch means for selectively connecting resistors of said first resistor bank in an arm of said bridge circuit;
a counter for actuating said first switch means as a function of the count state of said counter;
first storage means for storing the count state of said counter;
comparator means for producing an output signal when said bridge circuit is balanced and fixing the count state in said first storage means;
means for connecting said count state from said first storage means as one signal of said transmission link and representing said probe resistance;
means for producing a reference signal for said counter;
a plurality of resistors connected as a second resistor bank;
second switch means for selectively connecting resistors of said second resistor bank as an input to said monitor;
second storage means for actuating said second switch means as a function of the count state of said counter; and
means for connecting said count state from said transmission link and said reference signal to said second storage means as inputs for fixing the switches in said second switch means to selectively connect said second resistor bank identically to the connection of said first resistor bank.

2. A system as defined in claim 1 wherein the contents of said first storage means continuously changes as said count state changes, and including:
- means for connecting said comparator means output signal to said counter for stopping counting; and
- means for transferring the contents of said first storage means to said transmission link after said counter has stopped counting.

3. A system as defined in claim 2 wherein said counter has a parallel output to said first switch means and first storage means, and said first storage means has a serial output to said transmission link.

4. A telemetering system for transmitting temperature information between first and second temperature probes and a temperature monitor, each of said probes including a resistor with the resistance thereof varying as a function of its temperature, including in combination:
- a multisignal transmission link having transmitter and receiver;
- a first bridge circuit including means for connecting said first probe resistor in an arm of said first bridge circuit;
- a plurality of resistors connected as a first resistor bank;
- first switch means for selectively connecting resistors of said first resistor bank in an arm of said first bridge circuit;
- a first counter for actuating said first switch means as a function of the count state of said first counter;
- first storage means for storing the count state of said first counter;
- first comparator means for producing an output signal when said first bridge circuit is balanced and fixing the count state in said first storage means;
- a second bridge circuit including means for connecting said second probe resistor in an arm of said second bridge circuit;
- means for producing a reference signal for said counter;
- a plurality of resistors connected as a second resistor bank;
- second switch means for selectively connecting resistors of said second resistor bank in an arm of said second bridge circuit;
- a second counter for actuating said second switch means as a function of the count state of said second counter;
- second storage means for storing the count state of said second counter;
- second comparator means for producing an output signal when said second bridge circuit is balanced and fixing the count state in said second storage means;
- means for connecting said count states from said first and second storage means as one signal of said transmission link and representing said first and second probe resistances;
- a plurality of resistors connected as a third resistor bank;
- third switch means for selectively connecting resistors of said third resistor bank as an input to said monitor;
- third storage means for actuating said third switch means as a function of the count state of said first counter;
- first means for connecting one count state from said transmission link and said reference signal to said third storage means as inputs for fixing the switches in said third switch means;
- a plurality of resistors connected as a fourth resistor bank;
- fourth switch means for selectively connecting resistors of said fourth resistor bank as an input to said monitor;
- fourth storage means for actuating said fourth switch means as a function of the count state of said second counter; and
- second means for connecting the other count state from said transmission link and said reference signal to said fourth storage means as inputs for fixing the switches in said fourth switch means.

5. A telemetering system for transmitting resistance values between a first variable resistor and a monitor, including in combination:
- a transmission link having transmitter and receiver;
- a bridge circuit including means for connecting said first variable resistor in an arm of said bridge circuit;
- second variable resistance means;
- first means for connecting said second variable resistance means in an arm of said bridge circuit;
- a counter for actuating said first means for connecting as a function of the count state of said counter;
- first storage means for storing the count state of said counter;
- comparator means for producing an output signal when said bridge circuit is balanced and fixing the count state in said first storage means;
- means for connecting said count state from said first storage means as one signal of said transmission link and representing said first variable resistor;
- means for producing a reference signal for said counter;
- third variable resistance means;
- second means for connecting said third variable resistance means as an input to said monitor;
- second storage means for actuating said second means for connecting as a function of the count state of said counter; and
- means for connecting said count state from said transmission link and said reference signal as inputs for fixing said third variable resistance means.

* * * * *

UNITED STATES PATENT AND TRADEMARK OFFICE
CERTIFICATE OF CORRECTION

PATENT NO. : 4,356,486

DATED : October 26, 1982

INVENTOR(S) : Mount

It is certified that error appears in the above-identified patent and that said Letters Patent are hereby corrected as shown below:

Column 1 line 60 "end" should be --and--

Column 3 line 27 after electrodes insert --are--

Column 6 line 8 "control" should be --channel-- line 18 "(bits 01∝14)" should be --(bits 0-14)-- line 34 "$Ag = (3.3333 \times 10^{-4} - 1.1111 \times 10^{-1})A28 = 1.7360 \times 10^{-6}$" should be --$Ag = (3.3333 \times 10^{-4} - 1.1111 \times 10^{-4})A28 = 1.7360 \times 10^{-6}$-- line 47 "swtiched" should be --switched--

Column 9 line 41 "$k_1 p(t) + (k_1 l_3/k_2) A P_0,$" should be --$k_1 p(t) + (k_1 k_3/k_2) A P_0,$--

UNITED STATES PATENT AND TRADEMARK OFFICE
CERTIFICATE OF CORRECTION

PATENT NO. : 4,356,486

DATED : October 26, 1982

INVENTOR(S) : Mount

It is certified that error appears in the above-identified patent and that said Letters Patent are hereby corrected as shown below:

Column 9 line 52 "A/D" should be --A/D-- line 55 "as" should be --is--

Signed and Sealed this

Thirty-first Day of May 1983

[SEAL]

Attest:

DONALD J. QUIGG

Attesting Officer

Acting Commissioner of Patents and Trademarks